(12) United States Patent
Dale et al.

(10) Patent No.: US 8,507,257 B2
(45) Date of Patent: Aug. 13, 2013

(54) COMBINED THERMAL DEVICES FOR THERMAL CYCLING

(75) Inventors: Gregory A. Dale, Gaithersburg, MD (US); Shulin Zeng, Gaithersburg, MD (US); Kenton C. Hasson, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 36 days.

(21) Appl. No.: 12/966,583

(22) Filed: Dec. 13, 2010

(65) Prior Publication Data
US 2011/0081136 A1    Apr. 7, 2011

Related U.S. Application Data

(62) Division of application No. 11/771,067, filed on Jun. 29, 2007, now Pat. No. 7,851,185.

(60) Provisional application No. 60/806,440, filed on Jun. 30, 2006.

(51) Int. Cl.
*C12M 1/00*    (2006.01)

(52) U.S. Cl.
USPC ........................................... 435/283.1

(58) Field of Classification Search
None
See application file for complete search history.

(56) References Cited

U.S. PATENT DOCUMENTS

| | | | |
|---|---|---|---|
| 4,989,446 A | 2/1991 | Conti |
| 5,455,175 A | 10/1995 | Wittwer et al. |
| 5,498,392 A | 3/1996 | Wilding et al. |
| 5,716,825 A | 2/1998 | Hancock et al. |
| 5,972,667 A | 10/1999 | Conia et al. |
| 6,210,882 B1 | 4/2001 | Landers et al. |
| 6,218,126 B1 | 4/2001 | Yasuda et al. |
| 6,361,953 B1 | 3/2002 | Yasuda et al. |
| 6,391,541 B1 | 5/2002 | Petersen et al. |
| 6,403,037 B1 | 6/2002 | Chang et al. |
| 6,413,766 B2 | 7/2002 | Landers et al. |
| 6,413,780 B1 | 7/2002 | Bach et al. |
| 6,440,724 B2 | 8/2002 | Bertling |
| 6,551,841 B1 | 4/2003 | Wilding et al. |
| 6,605,475 B1 | 8/2003 | Taylor et al. |
| 6,713,297 B2 | 3/2004 | McMillan et al. |
| 6,716,584 B2 | 4/2004 | Yasuda et al. |
| 6,734,401 B2 | 5/2004 | Bedingham et al. |
| 6,762,049 B2 | 7/2004 | Zou et al. |
| 6,783,934 B1 | 8/2004 | McMillan et al. |

(Continued)

FOREIGN PATENT DOCUMENTS

| | | |
|---|---|---|
| WO | 9641864 | 12/1996 |
| WO | 9809728 A1 | 3/1998 |
| WO | 03102226 A1 | 12/2003 |

OTHER PUBLICATIONS

Slyadnev et al. Photothermal temperature control of a chemical reaction on a microchip using an infrared diode laser. Anal. Chem. 73:4037-4044 (2001).*

(Continued)

*Primary Examiner* — Samuel Woolwine

(74) *Attorney, Agent, or Firm* — Rothwell, Figg, Ernst & Manbeck, P.C.

(57) ABSTRACT

The invention relates to systems and methods including a combination of thermal generating device technologies to achieve more efficiency and accuracy in PCR temperature cycling of nucleic samples undergoing amplification.

4 Claims, 6 Drawing Sheets

(56) References Cited

U.S. PATENT DOCUMENTS

| | | |
|---|---|---|
| 6,787,314 B2 | 9/2004 | Yasuda et al. |
| 6,889,468 B2 | 5/2005 | Bedinhgam et al. |
| 6,893,823 B2 | 5/2005 | Yasuda et al. |
| 6,924,971 B2 | 8/2005 | Satsu et al. |
| 6,960,437 B2 | 11/2005 | Enzelberger et al. |
| 6,987,253 B2 | 1/2006 | Bedingham et al. |
| 7,056,387 B2 | 6/2006 | van der Steur |
| 7,101,509 B2 | 9/2006 | Chang et al. |
| 7,151,167 B2 | 12/2006 | Gjerde et al. |
| 2001/0010917 A1 | 8/2001 | Bertling |
| 2001/0029017 A1 | 10/2001 | Yasuda et al. |
| 2002/0029036 A1 | 3/2002 | Goble et al. |
| 2002/0031768 A1 | 3/2002 | McMillan et al. |
| 2002/0047003 A1 | 4/2002 | Bedingham et al. |
| 2002/0048771 A1 | 4/2002 | Yasuda et al. |
| 2002/0197603 A1 | 12/2002 | Chow et al. |
| 2003/0073229 A1 | 4/2003 | Greenstein et al. |
| 2003/0104466 A1 | 6/2003 | Knapp et al. |
| 2003/0124506 A1 | 7/2003 | Bedingham et al. |
| 2004/0053290 A1 | 3/2004 | Terbrueggen et al. |
| 2004/0067051 A1 | 4/2004 | Kylberg et al. |
| 2004/0096819 A1 | 5/2004 | McMillan et al. |
| 2004/0259237 A1 | 12/2004 | Kellogg et al. |
| 2005/0009070 A1 | 1/2005 | Arciniegas et al. |
| 2005/0012982 A1 | 1/2005 | Behfar |
| 2005/0106585 A1 | 5/2005 | Gjerde et al. |
| 2005/0158725 A1 | 7/2005 | Yukimasa et al. |
| 2005/0191708 A1 | 9/2005 | Saul et al. |
| 2005/0242091 A1 | 11/2005 | Bedingham et al. |
| 2005/0244933 A1 | 11/2005 | Panda et al. |
| 2005/0287661 A1 | 12/2005 | Landers |

OTHER PUBLICATIONS

Peake et al., "The polymerase chain reaction," J. Clin. Pathol. 42:673-676 (1989).

* cited by examiner

COMBINED THERMAL DEVICES FOR THERMAL CYCLING

This application is a divisional of patent application Ser. No. 11/771,067, filed Jun. 29, 2007, and issued as U.S. Pat. No. 7,851,185, which claims the benefit of Provisional Patent Application No. 60/806,440, filed on Jun. 30, 2006, which is incorporated herein by this reference.

BACKGROUND

1. Field of the Invention

The present invention relates to systems and methods for efficient thermal cycling in DNA amplification using a combination of energy sources, including electrical and/or magnetic (hereafter electromagnetic) radiation as an energy source.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA. With PCR, one can produce millions of copies of DNA starting from a single template DNA molecule. PCR includes phases of "denaturation," "annealing," and "extension." These phases are part of a cycle which is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

The PCR process phases of denaturing, annealing, and extension occur at different temperatures and cause target DNA molecule samples to replicate themselves. Temperature cycling (thermocyling) requirements vary with particular nucleic acid samples and assays. In the denaturing phase, a double stranded DNA (dsDNA) is thermally separated into single stranded DNA (ssDNA). During the annealing phase, primers are attached to the single stand DNA molecules. Single strand DNA molecules grow to double stranded DNA again in the extension phase through specific bindings between nucleotides in the PCR solution and the single strand DNA. Typical temperatures are 95° C. for denaturing, 55° C. for annealing, and 72° C. for extension. The temperature is held at each phase for a certain amount of time which may be a fraction of a second up to a few tens of seconds. The DNA is doubled at each cycle; it generally takes 20 to 40 cycles to produce enough DNA for the applications. To have good yield of target product, one has to accurately control the sample temperatures at the different phases to a specified degree.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Many detection methods require a determined large number of copies (millions, for example) of the original DNA molecule, in order for the DNA to be characterized. Because the total number of cycles is fixed with respect to the number of desired copies, the only way to reduce the process time is to reduce the length of a cycle. Thus, the total process time may be significantly reduced by rapidly heating and cooling samples to process phase temperatures while accurately maintaining those temperatures for the process phase duration.

Accordingly, what is desired is a system and method for rapidly and accurately changing process temperatures in PCR processes.

SUMMARY OF THE INVENTION

The present invention relates to systems and methods for rapid temperature change in microfluidic thermal cycling.

In one aspect, the present invention provides a method for cycling the temperature of a nucleic acid sample. In one embodiment, the method includes: (a) controlling a heating device to cause a temperature of the sample to be at or about a first desired temperature for at least a first time period; (b) after expiration of the first time period, increasing the output of an electromagnetic heating source to cause the temperature of the sample to be at or about a second desired temperature for at least a second time period; (c) during said second time period, lowering the amount of heat the heating device provides to the sample; and (d) immediately after expiration of the second time period, lowering the output of the electromagnetic heating source and controlling the heating device to cause the temperature of the sample to be at or about a third desired temperature for a third time period, wherein the first temperature is less than the second temperature and the third temperature is less than the first temperature. In some embodiments, steps (a) through (d) occur while the sample is flowing through a channel (e.g., a microfluidic channel).

In another embodiment, the method includes: heating the sample to a first temperature for a first time period using a thermoelectric device; heating the sample to a second temperature for a second time period using primarily an electromagnetic heat source; cooling the sample to a third temperature; and maintaining the third temperature for a third time period using the thermoelectric device, wherein the second temperature is higher than the first and the first temperature is higher than the third.

In another embodiment, the method includes: (a) heating the nucleic acid sample to about a first temperature; (b) after heating the sample to about the first temperature, maintaining the temperature of the sample at about the first temperature for a first period of time; (c) after expiration of the first period of time, heating the sample to about a second temperature; (d) after heating the sample to the second temperature, maintaining the temperature of the sample at about the second temperature for a second period of time; (e) after expiration of the second period of time, cooling the sample to about a third temperature; and (f) after cooling the sample to the third temperature, maintaining the temperature of the sample at about the third temperature for a third period of time, wherein the first temperature is less than the second temperature and greater than the third temperature, and the step of heating the sample to the second temperature consists primarily of using one or more non-contact heating elements to heat the sample to the second temperature.

In another aspect, the present invention provides a system for cycling the temperature of a nucleic acid sample. In one embodiment, the system includes: a nucleic acid sample container operable to receive a nucleic acid sample; a first heating device; and a second heating device, wherein the first heating device is configured to heat the nucleic acid sample to at least about a first temperature, the second heating device is configured to heat the nucleic acid sample to a second and third temperature, the first temperature is associated with a denaturing phase of a PCR process, the first heating device is a non-contact heating device, and the second heating device is a contact heating device.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of a reference number identifies the drawing in which the reference number first appears.

DETAILED DESCRIPTION OF PREFERRED EMBODIMENTS

Figure 1:
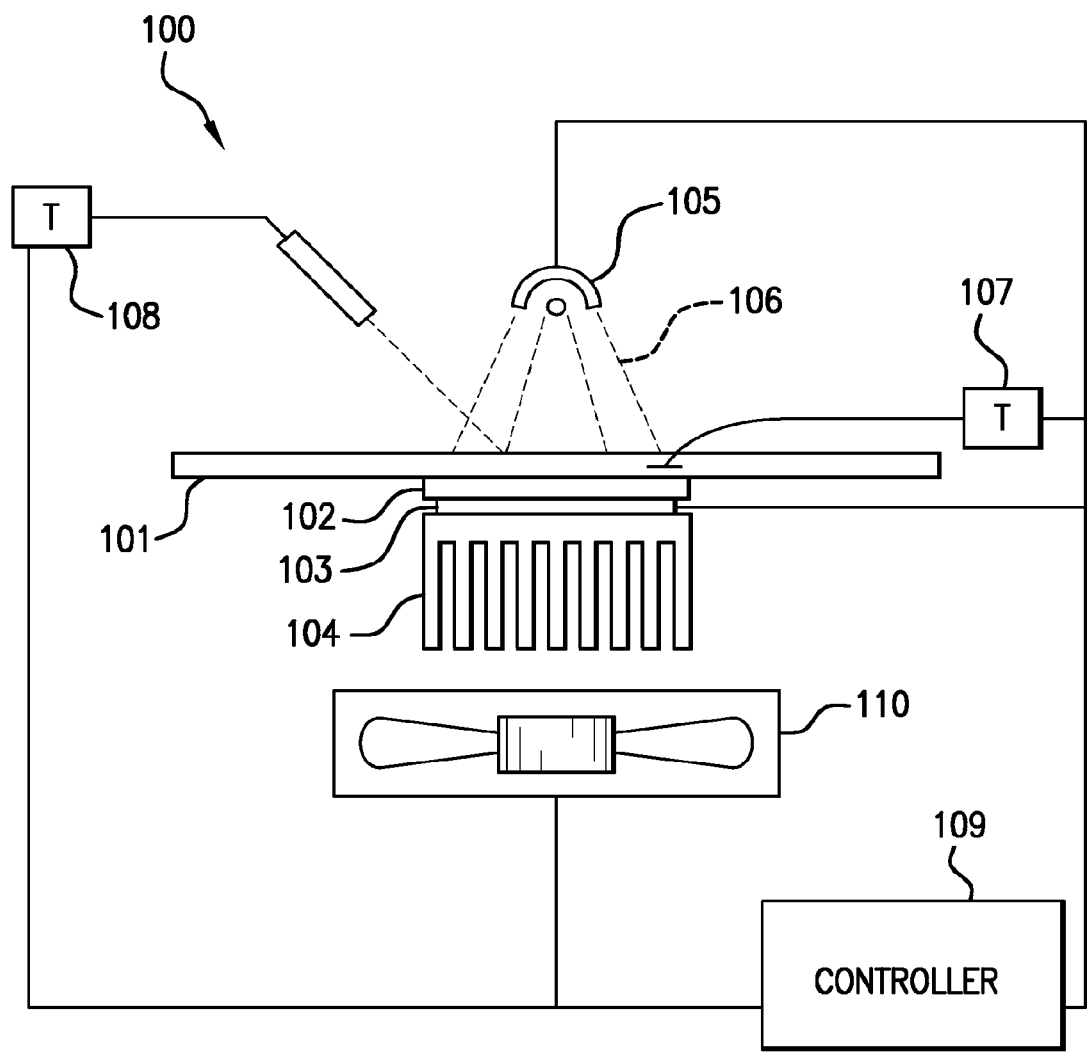
FIG. 1 depicts an apparatus in accordance with an exemplary embodiment of the invention.

With reference to FIG. 1, an exemplary embodiment of an apparatus 100 relating to the present invention may include: a microfluidic device 101 or other device for containing a sample containing a nucleic acid and PCR reagents (which PCR reagents may include PCR primers, dNTPs, polymerase enzymes, salts, buffers, surface-passivating agents, and the like), a heat spreader 102, a heating device 103, a heat sink 104, an electromagnetic heat source 105, a contact temperature sensing device 107, a non-contact temperature sensing device 108, a controller 109 and a fan 110.

In some embodiments, device 101 includes a microfluidic channel configured to receive the sample. The sample may flow through the channel as its temperature is cycled, as described herein. Moving the sample through the microfluidic channel can be accomplished by a variety of methods, for example, via conventional methods of pressure-driven flow (e.g., using a pump to create a pressure differential) and the flow rates can vary, for example between 10 nanoliters per minute to 1 ml per minute.

In the embodiment illustrated, heating device 103 is thermally in contact with the microfluidic device 101 through the metal heater spreader 102. Device 103 may be implemented using a thermoelectric cooler (TEC) (also referred to as a Peltier device), a resistive heater, a chemical heater, or other heating device. A suitable TEC may be available from Melcor Corporation of Trenton, N.J. (see part number HT6-6-21X43). In some embodiments, heating device 103 may have a different temperature resolution than heat source 105. More specifically, in some embodiments, heating device 103 may have a finer temperature resolution than heat source 105.

As mentioned above, device 103 may be implemented using a Peltier device, a widely used component in laboratory instrumentation and equipment, well known among those familiar with such equipment, and readily available from commercial suppliers such as Melcor. A Peltier device is a solid-state device that can function as a heat pump, such that when an electric current flows through two dissimilar conductors, the junction of the two conductors will either absorb or release heat depending on the direction of current flow. A typical Peltier device consists of two ceramic or metallic plates separated by a semiconductor material, such as bismuth telluride. The direction of heat flow is a function of the direction of the electric current and the nature of the charge carrier in the semiconductor (i.e., n-type or p-type). Peltier devices can be arranged and/or electrically connected in an apparatus of the present invention to heat or to cool a PCR process taking place in microfluidic device 101.

The size of heat spreader 102 is related to the sizes of the heating device 103 and microfluidic device 101. In an exemplary embodiment, a heat spreader of 20 mm×40 mm is used. Heat sink 104 removes waste heat from heating device 103. The assembly comprising the heat sink 104, heating device 103, and heater spreader 102 may be screwed together, bonded together, or clamped in place. Thermal coupling may be enhanced by the use of thermally conductive adhesives, greases, pastes, thermoconducting pads (e.g., a SIL-PAD product available from the Berquist Company of Chanhassen, Minn.).

A switchable fan 110 may be used to increase airflow towards the assembly and/or heat sink 104 in particular. The fan 110 and heat sink 104 can function together to quickly remove heat from the assembly. In some embodiments, fan 110 may be left on continuously during for an entire PCR process.

Electromagnetic heat source 105 may radiate energy 106 directed toward the microfluidic device 101 surface. A suitable electromagnetic heat source is any device which generates an electric and/or magnetic field which may be used to heat microfluidic device 101. An exemplary electromagnetic heat source 105 may be an infrared source including a tungsten filament bulb, such as one from the GE XR series, or a laser. Heat source 105 may be located ½ of an inch or less to twelve inches or more from the surface of microfluidic device 101. Preferably, heat source 105 is located at an angle so as to facilitate real-time PCR monitoring of the microfluidic zone and is located between about 2-6 inches from the surface of device 101.

Contact temperature sensing device 107 may be located inside or on the microfluidic device 101 surface. Suitable temperature sensors include a thin film wire, embedded wire, thermocouple, RTD, resistor, or solid state device. In some embodiments, a temperature measuring sensor available from Analog Devices is used to implement device 107 (e.g., the Analog Devices AD590 temperature transducer may be used). In some embodiments, a non-contact temperature sensing device 108, such as a pyrometer manufactured by Mikron, may be used in addition to or instead of contact temperature sensing device 107.

Controller 109 may be used to energize and deenergize heating device 103 and electromagnetic heat source 105 in a thermostatic fashion such that the temperature sensed by sensor 107 and/or 108 (e.g., the temperature of a region of microfluidic device 101) is at, or approximately at, a desired temperature for a desired period of time. Controller 109 include one or more computers or other programmable devices which may be programmed to control heating device 103, electromagnetic heat source 105, and/or fan 111 in response to the expiration of a timer and temperature measurements from contact temperature sensor 107 and/or non-contact temperature sensor 108.

Figure 2:
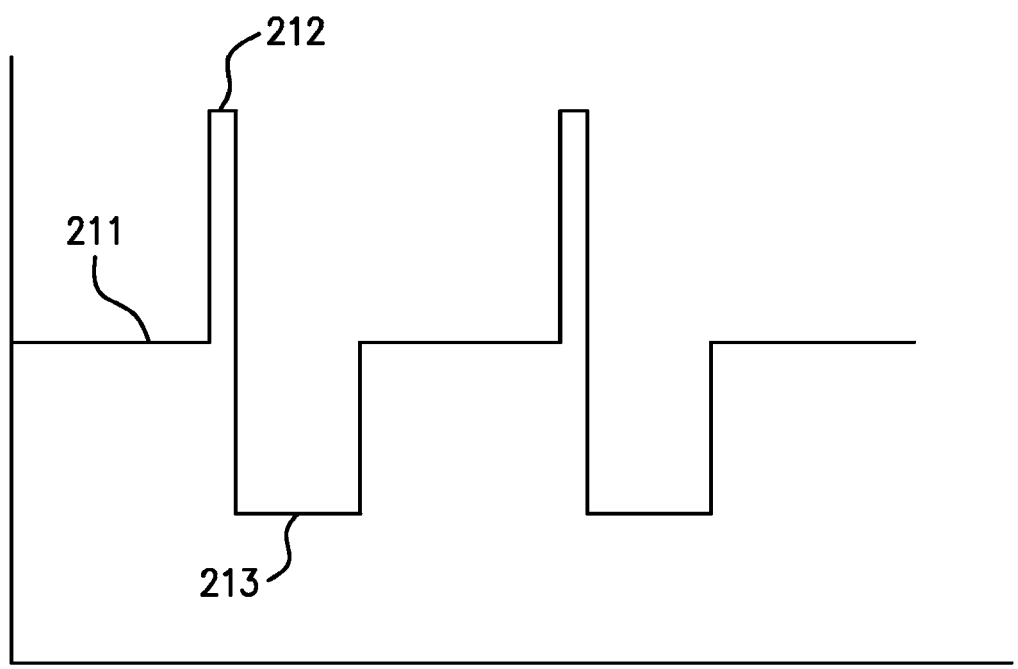
FIG. 2 depicts an exemplary desired PCR temperature cycle.

FIG. 2 depicts an exemplary desired PCR cycle. In this exemplary cycle, phase 211 is the extension phase, phase 212 is the denaturation phase, and phase 213 is the annealing phase. Typically, the denaturation phase 212 requires less precision of temperature and time control, provided that a minimum temperature point is achieved homogeneously in the microfluidic device 101.

In a preferred embodiment, controller 109 is programmed to use primarily heating device 103 to heat and/or cool microfluidic device 101 during extension phase 211 and annealing phase 213. That is, in some embodiments, source 105 may be turned "off" during the extension phase and annealing phase or may output a lower level of radiation 106 during these phases than it outputs during denaturation phase 212. Controller 109 is operable to energize the heating and/or cooling ability of heating device 103 such that the desired temperatures are quickly reached and maintained for the desired times. For example, an extension phase 211 may have a duration of about 5 seconds and a desired temperature of about 72° C. An exemplary annealing phase 213 may have a desired duration of 2 seconds and a desired temperature of about 55° C.

In the preferred embodiment, electromagnetic heat source 105 provides to microfluidic device 101 a greater amount of heat during the denaturation phase 212 than during the other two phases of the PCR cycle. Additionally, during denaturation phase 212, device 103 may be operated to provide less heat to device 101 than device 103 is configured to provide to device 101 during the other two phases of the PCR cycle. Accordingly, in some embodiments, device 103 may actually draw heat from device 101 during denaturation phase 212. An exemplary desired denaturation phase 212 may last about 500 ms at a desired temperature of about 95° C.

Figure 3:
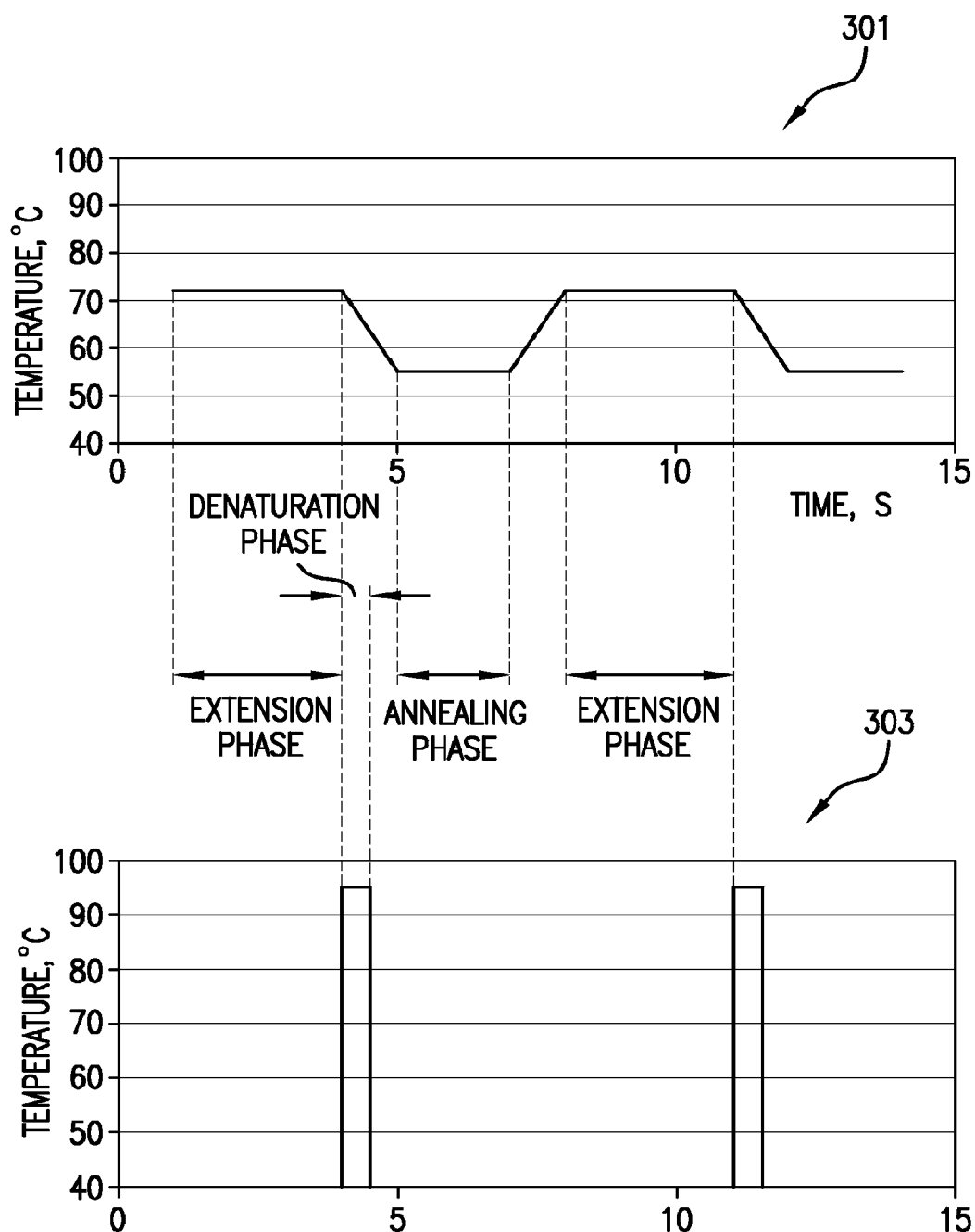
FIG. 3 depicts a temperature characteristic of a heating device and of an electromagnetic heating device.

FIG. 3 depicts exemplary plots of a heating device 103 temperature characteristic 301 and source 105 temperature characteristic 303. Characteristic 301 illustrates that the heating device 103 is controlled by the controller 109 such that the desired temperature control of the sample for the extension phase 211 and annealing phase 213 is substantially provided through the functioning of the heating device 103. Characteristic 303 illustrates that the electromagnetic heat source 105 is controlled by the controller 109 such that the desired temperature control of the sample for denaturation phase 212 is substantially provided through the functioning of the electromagnetic heat source 105.

Figure 4:
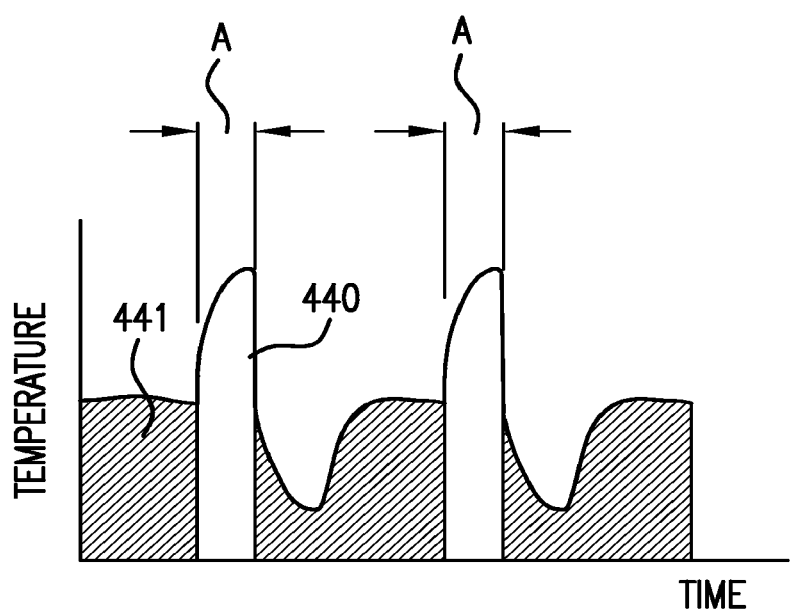
FIGS. 4 and 5 depict a temperature cycle.
Figure 5:
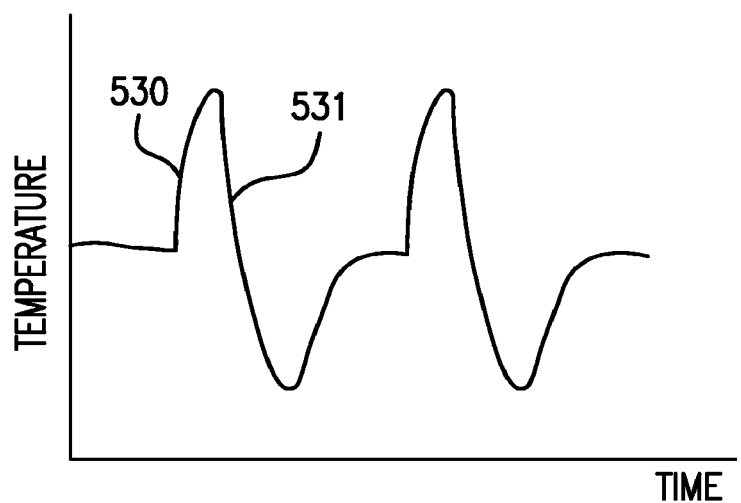

FIGS. 4 and 5 depict time and temperature graphs for a sample contained in device 101 when heat sources 103 and 105 are operated according to the diagram shown in FIG. 3. Shaded area 441 represents the part of the cycle for which device 103 provides thermal input. Period A, which occurs in area 440, represents the duration of an energy input from source 105.

Accordingly, and with reference to FIG. 5, fast thermal ramp/rise rates may be achieved as indicated by slope 530. Furthermore, high cooling rates may be achieved as indicated by slope 531.

Figure 6:
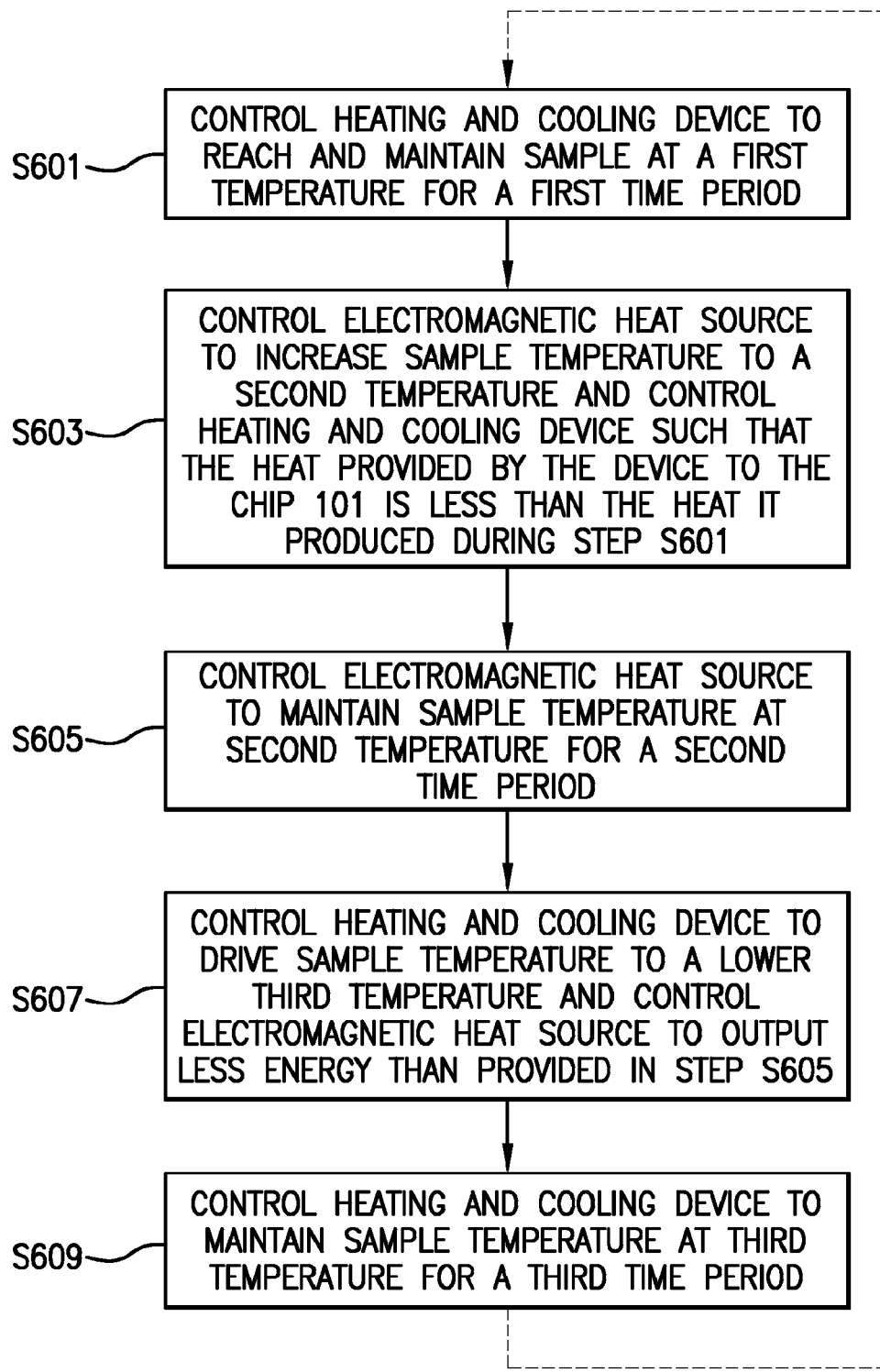
FIG. 6 depicts steps in an exemplary method in accordance with an embodiment of the present invention.

Referring now to FIG. 6, FIG. 6 is a flow chart illustrating a process, according to some embodiments of the invention, for cycling the temperature of a sample that is present in device 101.

The process may begin in step S601, where the controller controls thermostatically heating device 103 such that the extension phase temperature is reached and maintained for a desired duration of the extension phase 211. While step S601 is being performed, source 105 may be in an "off" state.

In step S603, which preferably does not occur until about immediately after the expiration of the desired extension phase duration, controller 109 increases the output of electromagnetic heat source 105. Preferably, the output of source 105 is raised to a level that causes the temperature of the sample to rapidly increase to the denaturation phase temperature.

In step 605, controller 109 may control thermostatically one or more of the heating and cooling devices of apparatus 100 so that the sample is kept at the denaturation phase temperature for the desired duration of the denaturation phase 212.

At or about the same time controller 109 causes heat source 105 to heat the sample to the denature temperature, controller 109 may control device 103 such that the heat provided by device 103 to device 101 is less than the heat device 103 provided to device 101 during step S601 (i.e., during extension phase 211).

In step S607, which preferably does not occur until about immediately after the expiration of the desired denature phase duration, controller 109 lowers the energy output (e.g., turns off) electromagnetic heat source 105 and controls heating device 103 such that the annealing phase temperature is reached. In some embodiments, step S607 includes using the cooling capability of the heating device to quickly drive the temperature of the sample down from the denaturation phase temperature to the annealing phase temperature as shown in ramp 531. In some embodiments, step S607 also includes activating and directing fan 110 at the microfluidic device 101 and/or heat sink 104 to drive the temperature down rapidly as shown in ramp 631.

In step S609, controller 109 may control thermostatically one or more of the heating and cooling devices of apparatus 100 so that the sample is kept at the annealing phase temperature for the desired duration of the annealing phase 213. For example, if a temperature sensor (e.g., sensor 107 or 108) indicates that the temperature of the sample is too low, then controller 109 may control a heat source (e.g., device 103 or source 105) to add more heat to the sample, and if a temperature sensor 108 indicates that the temperature of the sample is too low, then controller 109 may control device 103 so that it draws heat from the sample.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

Furthermore, one of skill in the art will recognize that temperatures enumerated in the following claims should be interpreted to mean "at or about" the enumerated temperature.

For the claims below the words "a" and "an" should be construed as "one or more."

What is claimed is:

1. A nucleic acid sample heating system, comprising:
   a nucleic acid sample container operable to receive a nucleic acid sample;
   a switchable fan;
   a heat sink;
   a heat spreader;
   a first heating device;
   a second heating device, and
   a controller; wherein
   the first heating device is configured to heat the nucleic acid sample to at least about a first temperature,
   the second heating device is configured to heat the nucleic acid sample to a second and third temperature,
   the first temperature is associated with a denaturing phase of a PCR process,
   the first heating device is a non-contact heating device, and
   the second heating device is a contact heating device.

2. The system of claim 1, wherein:
   the first heating device has a first temperature resolution;
   the second heating device has a second temperature resolution, and
   the second temperature resolution is finer than the first temperature resolution.

3. The system of claim 1, wherein the first heating device comprises a source configured to produce infra-red radiation and the second heating device is a Peltier heating element.

4. The system of claim 1, wherein the container comprises a microfluidic device having a microfluidic channel configured to receive the nucleic acid sample.

* * * * *